United States Patent [19]

Schmidt

[11] 4,307,475
[45] Dec. 29, 1981

[54] VACUUM CUSPIDOR

[75] Inventor: Theodore E. Schmidt, Carlton, Oreg.

[73] Assignee: A-Dec, Inc., Newberg, Oreg.

[21] Appl. No.: 82,041

[22] Filed: Oct. 5, 1979

Related U.S. Application Data

[62] Division of Ser. No. 877,898, Feb. 15, 1978, abandoned.

[51] Int. Cl.³ .............................................. A61C 17/04
[52] U.S. Cl. .............................................. 4/263; 4/264
[58] Field of Search .................... 4/263, 264; 137/403, 137/192

[56] References Cited

U.S. PATENT DOCUMENTS

| | | | |
|---|---|---|---|
| 604,218 | 5/1898 | Rosenberg | 4/264 |
| 1,948,523 | 2/1934 | Kahlert | 4/263 |
| 2,169,324 | 8/1939 | Monnot | 4/263 |
| 2,638,670 | 5/1953 | Wyne | 4/263 X |
| 2,760,596 | 8/1956 | Kellie | 137/192 X |
| 3,330,292 | 7/1967 | Lansky | 137/192 |
| 3,359,575 | 12/1967 | Nielsen | 4/263 |
| 3,384,907 | 5/1968 | Lappin et al. | 4/264 |
| 3,426,788 | 2/1969 | Bassett | 137/403 |
| 3,653,078 | 4/1972 | Buchtel et al. | 4/263 |
| 3,654,953 | 4/1972 | Hagdorn | 137/403 |

Primary Examiner—Henry K. Artis
Attorney, Agent, or Firm—Klarquist, Sparkman, Campbell, Leigh, Whinston & Dellett

[57] ABSTRACT

The specification discloses an improved dental cuspidor having a vacuum drain means. The specification also discloses a drain having a drain chamber of which one side is formed by a diaphragm so that when water reaches a given height in the chamber, the diaphragm actuates an air valve to drive a piston to open a drain valve to a vacuum drain.

1 Claim, 7 Drawing Figures

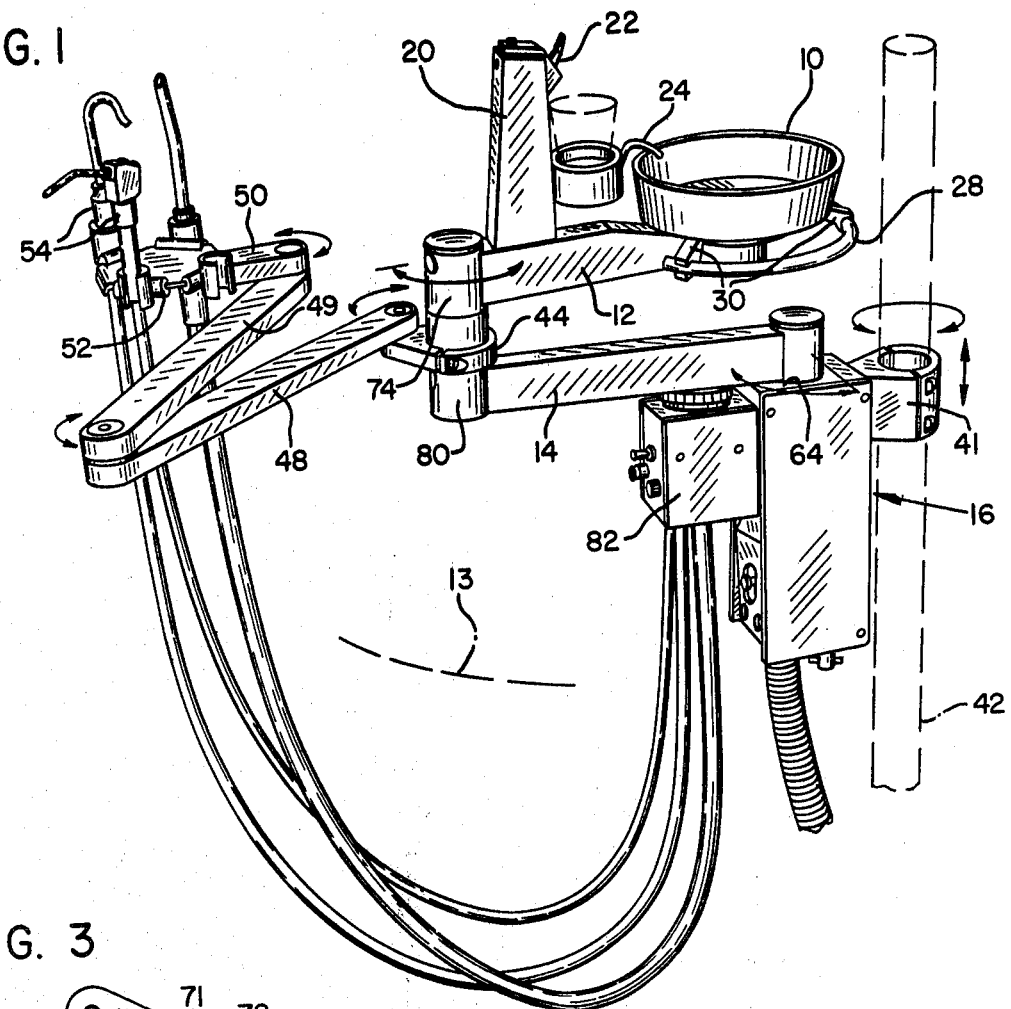
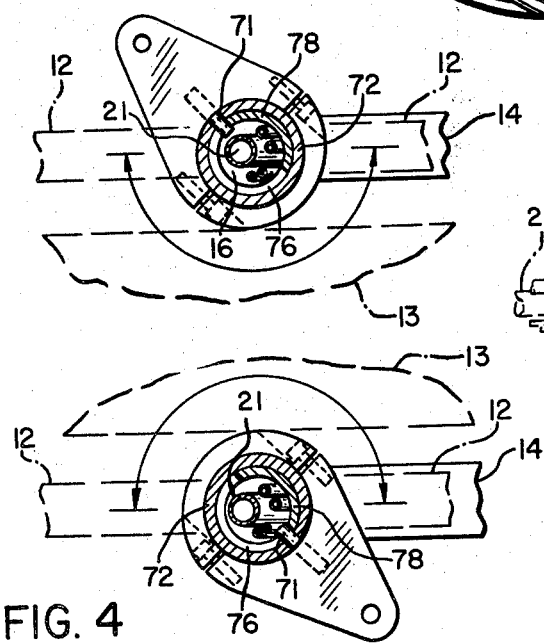
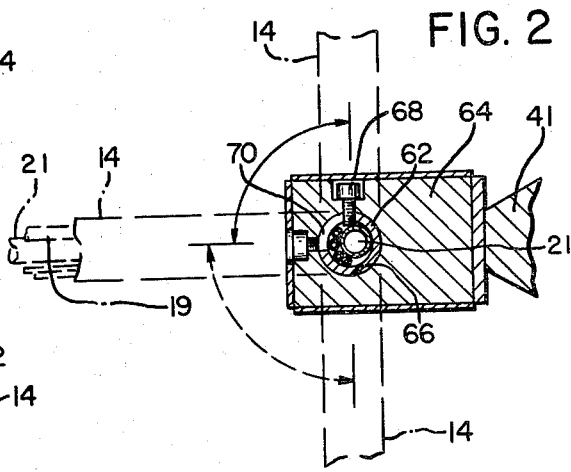

VACUUM CUSPIDOR

This application is a division of my prior co-pending application entitled "Improved Vacuum Cuspidor", Ser. No. 877,898, filed Feb. 15, 1978, now abandoned.

DESCRIPTION

This invention relates to an improved dental cuspidor and has for an object thereof the provision of a new and improved dental cuspidor.

Another object of the invention is to provide a dental cuspidor having a novel vacuum drain.

A further object of the invention is to provide a drain having a diaphragm forming one side of a trap and actuating a valve to open a piston driven valve to connect the trap to a drainline.

In the drawings:

FIG. 1 is a perspective view of an improved dental cuspidor forming one embodiment of the invention;

FIGS. 2, 3 and 4 are enlarged, fragmentary, horizontal sectional views of the cuspidor of FIG. 1;

Figure 7:
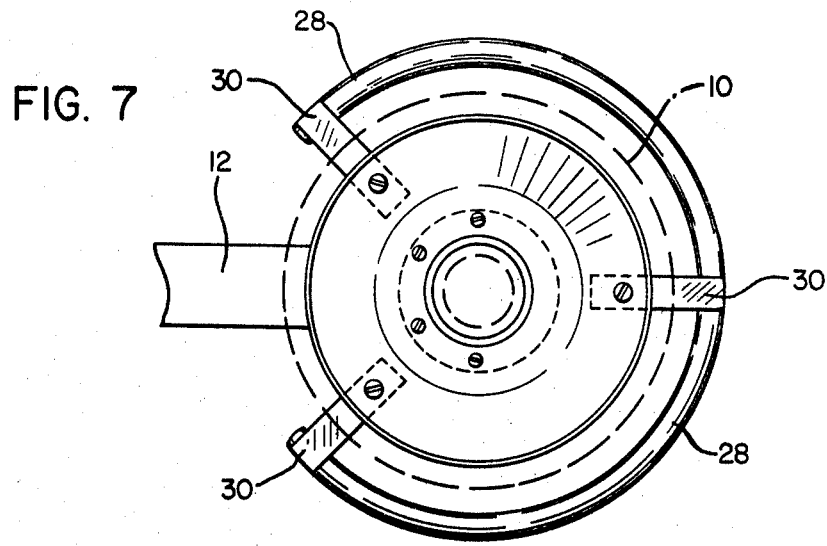
FIG. 7 is an enlarged fragmentary to plan view of the cuspidor of FIG. 1.

An improved dental cuspidor forming a specific embodiment of the invention includes a bowl 10 mounted by arms 12 and 14 for pivotal movement from a retracted position away from a patient in a dental chair 12 to any desired position over or adjacent the patient. The arm 14 is movable through ninety degrees and the arm 12 is movable through one hundred eighty degrees. The arms are tubular and form a drain line housing for a flexible hose 21 from the bowl to a vacuum drain 16 connected by a flexible hose 18 to a drain (not shown) via a vacuum unit (not shown). If desired, the hose 21 may be omitted and the arms 12 and 14 may house metal tubes coupled by a sealed rotary coupling. The arms also slope downwardly from the bowl. Small, flexible water lines 19 from a source (not shown) extend along the arms 14 and 12 to a dispensing fountain 20 controlled by a toggle switch type valve 22, the fountain being mounted on the arm 12. One line 19 supplies water to a nozzle 24 through a manually controlled shut-off valve (not shown). The nozzle supplies water to the bowl.

Spokes 30 extending radially of the bowl 10 and supported by the arm 12 carry an arcuate guard 28, which is substantially concentric to the bowl and is positioned radially outwardly from the outer perimeter of the bowl to act as a guard for the bowl. The guard also is a convenience handle for moving the bowl to any desired position. Vent and drain hoses 33 and 34 lead from a cup support 36 to a T-coupling 35 connecting two sections of the hose 21. The arm 12 is in the form of a heavy downwardly facing channel and is secured by a screw 37 to tubular elbow 74. A screw 38 secures a trap member 39 to the arm 12. A pan 41 fixed to the trap 39 and screws 43 secure the spokes 30 to the pan. A bushing 45 connects the hose 18 to the trap portion of the member 39.

Figure 5:
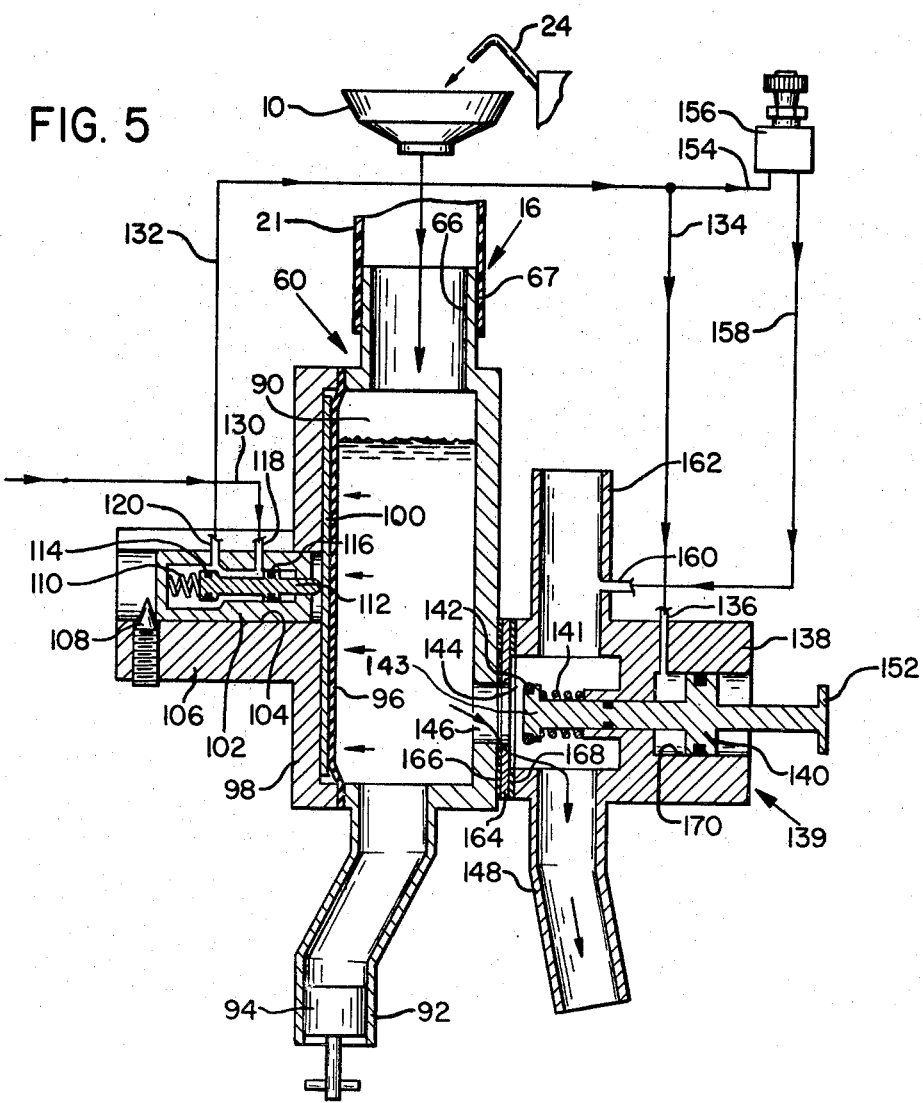
FIG. 5 is a fragmentary, vertical, sectional view of the drain of FIG. 1.

The vacuum drain 16 has a cylindrical housing 60 (FIG. 5) secured rigidly at any desired height or angle by a split clamp 41 to a post 42, and the arm 14 is pivotal on mounting block 64. A split clamp 44, secured to a boss portion 72 of the arm 14, carries arms 48, 49 and 50, carrying a rack 52 for instruments 54 for use by a dental assistant.

The housing encloses a drain body 60, and a cylindrical elbow tube 62 of the arm 14 mounted in and keyed to the block 64, is rotatable in the upper end of a bore 66 in the block 64 for ninety degree rotation as limited by a screw 68 extending into a slot 70 in the tube 62. Similarly, a pin 71 (FIG. 4) extending through the boss portion 77 of elbow 74 of the arm 12 and carried by the clamp 44 is movable in a slot 76 in lower portion 78 of the elbow 74 of the arm 12. A control box 82 for the instruments 54 is mounted on the housing.

The valve body 60 has a cylindrical chamber 90 and a bottom tube 92, which can be connected by a flexible hose (not shown) to a drain pipe (not shown) for gravity draining, or, as is shown, can be closed by a plug 94 to form a trap. A diaphragm 96, clamped between a cup 98 and the valve body 60, forms one side of the chamber 90 and carries a rigid disc 100. An air valve body 102 is adjustably positioned in bore 104 in boss 106 of the cup by a tapered screw 108. A spring 110 presses a plunger 112 in the valve body 102 into contact with the disc 100 and urges the plunger normally to a position in which a poppet valve 143 including an O-rings 114 and 116 close off an inlet port 118 from an outlet port 120.

Figure 6:
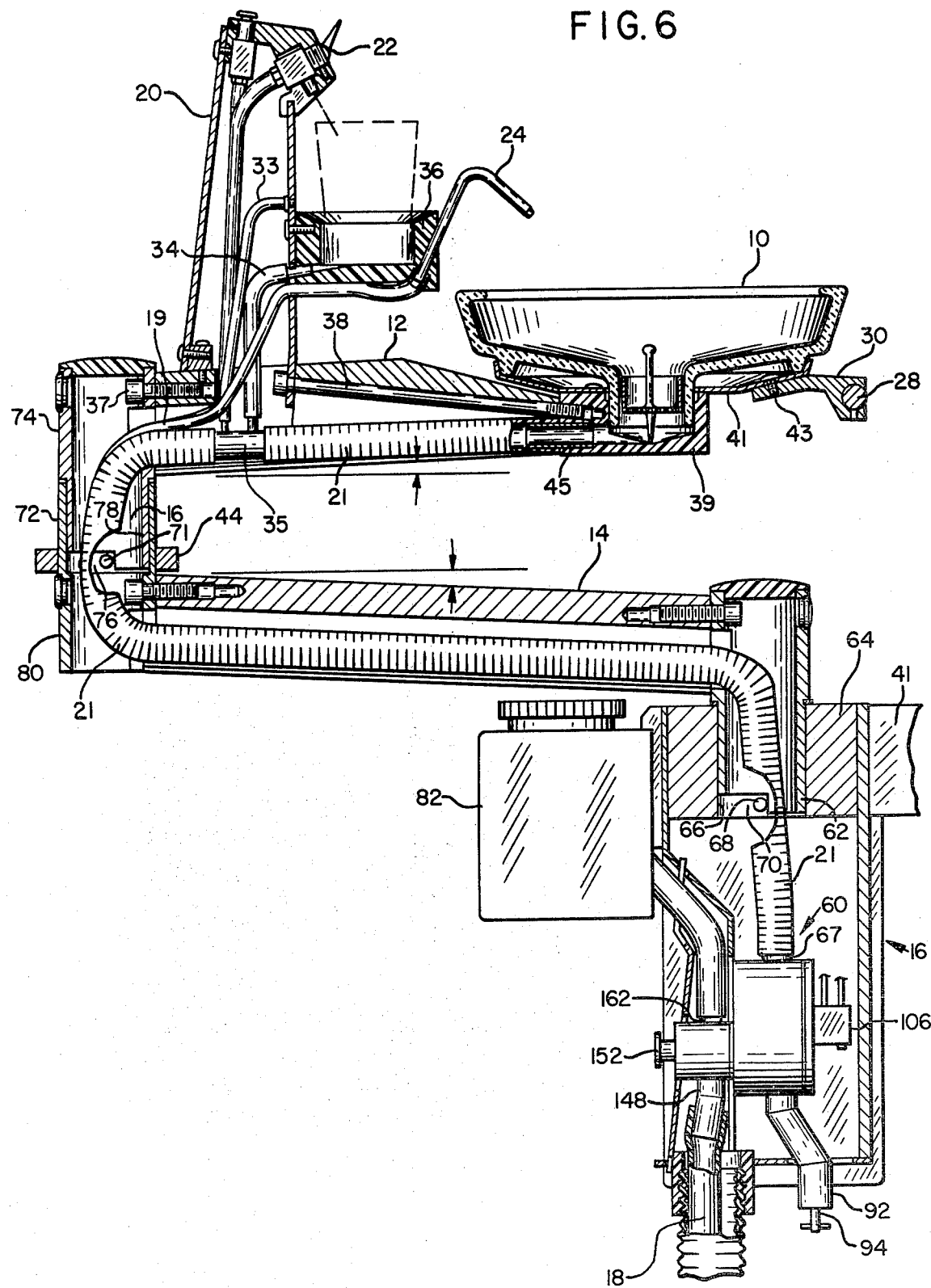
FIG. 6 is an enlarged vertical sectional view of the cuspidor of FIG. 1.

When water in the chamber 90 reaches a predetermined height, it moves the diaphragm 96 to the left sufficiently to move the plunger 112 to a position opening the port 118 to the port 120. Air under pressure supplied to the port 118 through a line 130 then flows through lines 132 and 134 to a port 136 in a vacuum drain valve body 138 of a drain valve 139 and moves a piston 140 to the right to move, against the action of spring 141, O-ring 142 away from valve seat 144 surrounding drain port 146 to connect the chamber 90 to a vacuum drain tube 148 connected to the flexible hose 18. The hose 18 is connected through a vacuum unit (not shown) to the drain of the building. A knob 152 is provided for manually opening the valve. A bleeder line 154 leads from the line 134 through a needle valve 156 to a line 158 leading to a port 160 in tube 162, which as shown in FIG. 6, is connected by a hose to control box 82. An adapter plate 164 is secured by screws (not shown) to the valve body 138 with a gasket 168 therebetween and the valve body 138 is secured by screws (not shown) to the body 60, with a gasket 166 therebetween. As will be apparent, because the vacuum line 148 is cut off by the poppet valve 143 and the water in the chamber 90, the cuspidor will be silent, even for those brief periods when the poppet valve is open, thus, not distracting the dentist or the patient.

When the water level in the chamber 90 drops sufficiently, which will obviously be to a point above the lower edge of the bore 104, the spring 110 moves the plunger 112 to a closing position, the lines 134, 154 and 158 bleed off the air in counterbore 170 and the spring 141 closes the valve 139.

What is claimed is:

1. An improved dental cuspidor,
   a cuspidor bowl,
   a drain means for the cuspidor comprising a cylindrical trap body having an open vertical side,
   diaphragm means closing the vertical side,
   a drain opening in the side wall of said trap body,
   a poppet valve for closing said opening including a stem extending exteriorly of said body and adapted to be grasped manually for manual operation of said poppet valve,
spring means operatively connected to said poppet valve and biasing the same to closed position,
a cylinder encompassing said stem and a piston on said stem slidably engaging the cylinder wall,
a source of fluid under pressure connected to said cylinder to cause said piston to move said poppet valve to open position against the bias of said spring,
and valve means actuated by the diaphragm means for controlling the flow of fluid from said source to said cylinder.

* * * * *

UNITED STATES PATENT AND TRADEMARK OFFICE
CERTIFICATE OF CORRECTION

PATENT NO. : 4,307,475

DATED : December 29, 1981

INVENTOR(S) : Theodore E. Schmidt

It is certified that error appears in the above—identified patent and that said Letters Patent is hereby corrected as shown below:

Column 1, line 32, "12" should read -- 13 --.

Signed and Sealed this

Thirty-first Day of August 1982

[SEAL]

Attest:

Attesting Officer

GERALD J. MOSSINGHOFF

Commissioner of Patents and Trademarks